United States Patent
Lee et al.

(10) Patent No.: US 10,385,046 B1
(45) Date of Patent: Aug. 20, 2019

(54) PROCESSES FOR PREPARING BENZOTHIAZOL COMPOUNDS AND METHODS OF USING THE SAME FOR TREATING NEURODEGENERATIVE DISORDERS

(71) Applicant: 1ST Biotherapeutics, Inc., Gyeonggi-do (KR)

(72) Inventors: Jinhwa Lee, Gyeonggi-do (KR); Suyeon Jo, Gyeonggi-do (KR)

(73) Assignee: 1ST Biotherapeutics, Inc., Gyeonggi-do (KR)

( * ) Notice: Subject to any disclaimer, the term of this patent is extended or adjusted under 35 U.S.C. 154(b) by 0 days.

(21) Appl. No.: 16/357,642

(22) Filed: Mar. 19, 2019

(51) Int. Cl.
C07D 417/04 (2006.01)
(52) U.S. Cl.
CPC .................. *C07D 417/04* (2013.01)
(58) Field of Classification Search
CPC ................................... C07D 417/04
USPC ..................................... 546/270.1
See application file for complete search history.

(56) References Cited

U.S. PATENT DOCUMENTS

| | | | |
|---|---|---|---|
| 7,928,140 B2 | 4/2011 | Booker et al. | |
| 8,053,574 B2 | 11/2011 | Bruce et al. | |
| 9,505,784 B2 | 11/2016 | Choi et al. | |
| 2019/0100500 A1* | 4/2019 | Lee ...................... | C07D 277/82 |

FOREIGN PATENT DOCUMENTS

| | | |
|---|---|---|
| WO | WO-2007/095588 A1 | 8/2007 |
| WO | WO-2009/017822 A2 | 2/2009 |
| WO | WO-2009/133127 A1 | 11/2009 |
| WO | WO-10/008847 A2 | 1/2010 |
| WO | WO-10/100144 A1 | 9/2010 |

OTHER PUBLICATIONS

Hantschel, O., et al.; "Regulation of the C-ABL and BCR-ABL Tyrosine Kinases", Nature Reviews, Molecular Cell Biology, vol. 5, Jan. 2004, pp. 33-44.
Hebron, M. L., et al.; "Nilotinib reverses loss of dopamine neurons and improves motor behavior via autophagic degradation of a-synuclein in Parkinson's disease models", Human Molecular Genetics, 2013, vol. 22, No. 16, pp. 3315-3328.
Imam, S. Z., et al.; "Novel Regulation of Parkin Function through c-Abl-Mediated Tyrosine Phosphorylation: Implications for Parkinson's Disease", The Journal of Neuroscience, 31(1):pp. 157-163. 2011.
Imamura, K., et al.; "The Src/c-Abl pathway is a potential therapeutic target in amyotrophic lateral sclerosis", Science Translational Medicine, vol. 9, May 24, 2017, pp. 1-10.
Jellinger, K. A., et al., "Multiple system atrophy: pathogenic mechanisms and biomarkers", High Impact Review in Neuroscience, Neurology or Psychiatry Review Article, J Neural Transm., 2016, pp. 1-18.
Mahul-Mellier, A., et al.; "c-Abl phosphorylates a-synuclein and regulates its degradation: implication for a-synuclein clearance and contribution to the pathogenesis of Parkinson's disease", Human Molecular Genetics, 2014, vol. 23, No. 11, pp. 2858-2879.

* cited by examiner

*Primary Examiner* — Patricia L Morris
(74) *Attorney, Agent, or Firm* — Harness, Dickey & Pierce, P.L.C.

(57) ABSTRACT

The present disclosure provides a process for preparing (1S,2S)-2-fluoro-N-(6-(4-methylpyridin-3-yl)benzo[d]thiazol-2-yl) cyclopropanecarboxamide or a salt thereof, such as the compound of Formula (I), comprising:

Formula (I)

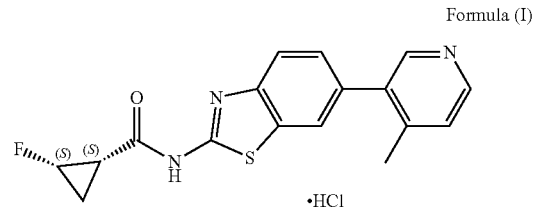

reacting Compound 1 as a starting material with Compound 2 in the presence of Pd(dppf)Cl$_2$ and 1,4-dioxane to form Compound 3; reacting Compound 3 with Compound 4 in the presence of HATU and DIPEA to produce Compound 5; and reacting Compound 5 with hydrochloric acid to produced Formula (I).

14 Claims, 14 Drawing Sheets

PROCESSES FOR PREPARING BENZOTHIAZOL COMPOUNDS AND METHODS OF USING THE SAME FOR TREATING NEURODEGENERATIVE DISORDERS

FIELD

The present disclosure generally relates to process and methods for preparing compounds having enzyme inhibitory activity and methods of using the compounds for treating neurodegenerative disorders.

BACKGROUND

α-Synuclein is part of a large family of proteins including β- and γ-synuclein and synoretin. α-Synuclein is expressed in the normal state associated with synapses and is believed to play a role in neural plasticity, learning and memory. Several studies have implicated α-synuclein with a central role in Parkinson disease pathogenesis. Molecular changes in the α-synuclein protein that increase protein misfolding and aggregation have a direct role in disease pathogenesis. Aggregation of α-synuclein contributes to the formation of Lewy bodies and neurites, the pathologic hallmarks of Parkinson disease and α-synucleinopathies. Activation of tyrosine kinase c-abl contributes to α-synuclein-induced neurodegeneration.

The tyrosine kinase c-abl is tightly regulated non-receptor protein tyrosine kinase involved in a wide range of cellular processes, including growth, survival and stress response (*Nat Rev Mol Cell Biol,* 2004, 5:33-44) and c-abl involved in regulation several cellular processes and has implicated in the development of the central nervous system by controlling neurogenesis. More recently, increasing evidence from various experimental model systems has also revealed that c-abl is activated in neurodegenerative disease such as Alzheimer's disease, Parkinson's disease, Niemann-Pick type C diseases and tauopathies. (*Human Molecular Genetics,* 2014, Vol. 23, No. 11)

The stress-signaling non-receptor tyrosine kinase c-abl links parkin to sporadic forms of Parkinson's disease via tyrosine phosphorylation. Tyrosine phosphorylation of parkin by c-abl is a major post-translational modification that leads to loss of parkin function and disease progression in sporadic Parkinson disease. Inhibition of c-abl offers new therapeutic opportunities for blocking Parkinson disease progression. (*The Journal of Neuroscience.* 2011, 31(1): 157-163) Amyotrophic lateral sclerosis (ALS) is a fatal neurodegenerative disease characterized by progressive death of motor neurons. Knockdown of c-abl with small interfering RNAs (siRNAs) also rescued ALS motor neuron degeneration. (Imamura et al., *Sci. Transl. Med.* 9, 2017) Multiple System Atrophy (MSA) is a rare, rapidly progressive neurodegenerative disease without any current treatment. In MSA there is accumulation of α-synuclein in the neurons and oligodendrocytes of the substantia nigra, striatum, olivopontocerebellar structures and spinal cord. (*J Neural Transm Vienna Austria* 1996. 2016:123(6)).

Administration of the tyrosine kinase inhibitor nilotinib decreases c-abl activity and ameliorates autophagic clearance of α-synuclein in transgenic and lentiviral gene transfer models. Activation of c-abl in the mouse forebrain induces neurodegeneration in the hippocampus and striatum. Therefore, an increase in c-abl activity via phosphorylation may be associated with the α-synuclein pathology detected in Parkinson disease and other neurodegenerative disease. (*Hum Mol Genet.* 2013 Aug. 15).

U.S. Ser. No. 16/148,165 describes benzothiazol compounds as a c-abl inhibitor that is useful for the treatment of a disease or disorders such as α-synucleinopathy, Parkinson disease, Alzheimer disease, ALS, Dementia with Lewy body and MSA. The present disclosure describes a process and method for preparing and purifying the benzothiazol compound. The method may avoid excessive formation of byproducts during the reaction, improve the yield, and/or simplify the purification process.

SUMMARY

The present disclosure provides processes and methods for preparing (1S,2S)-2-fluoro-N-(6-(4-methylpyridin-3-yl) benzo[d]thiazol-2-yl) cyclopropanecarboxamide and salts thereof, having c-abl kinase inhibitory activity, compositions comprising the compound, and methods of using the compound to treat various diseases including a neurodegenerative disease.

In an embodiment, there is provided a process for preparing (1 S,2S)-2-fluoro-N-(6-(4-methylpyridin-3-yl)benzo [d]thiazol-2-yl) cyclopropanecarboxamide and salts thereof, comprising:

Step 1: reacting Compound 1 as a starting material with Compound 2 in the presence of Pd(dppf)Cl$_2$ and 1,4-dioxane to form Compound 3; and

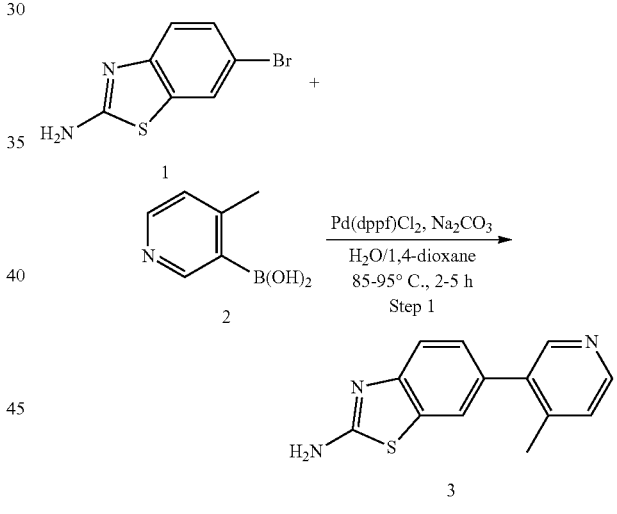

Step 2: reacting Compound 3 with Compound 4 in the presence of HATU and DIPEA to produce Compound 5

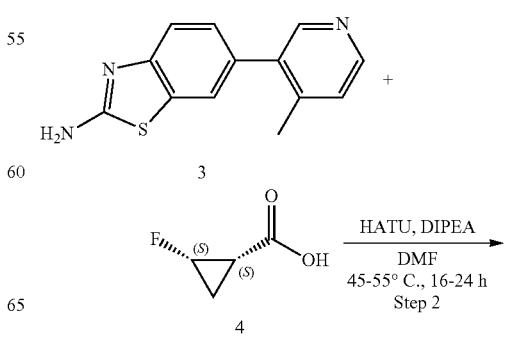

-continued

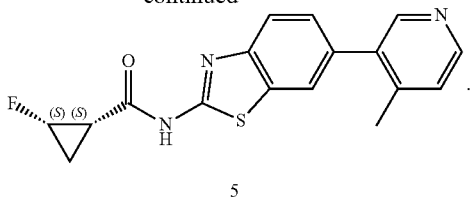

5

In another embodiment, there is provided a method for preparing a salt of Compound 5, wherein the method further comprises a step of reacting Compound 5 with an acid to form the salt of Compound 5.

In a particular embodiment, the method is to prepare the compound of Formula (I), wherein the method further comprises:

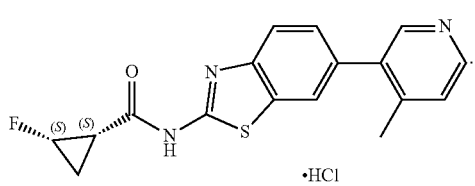
·HCl
(I)

Step 3: reacting Compound 5 with hydrochloric acid 35% to form the compound of Formula (I).

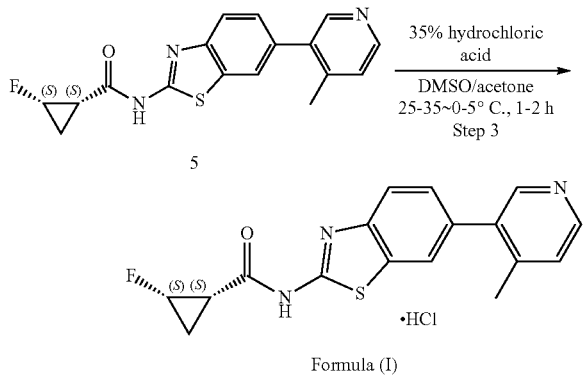

Formula (I)

DETAILED DESCRIPTION

Figure 1:
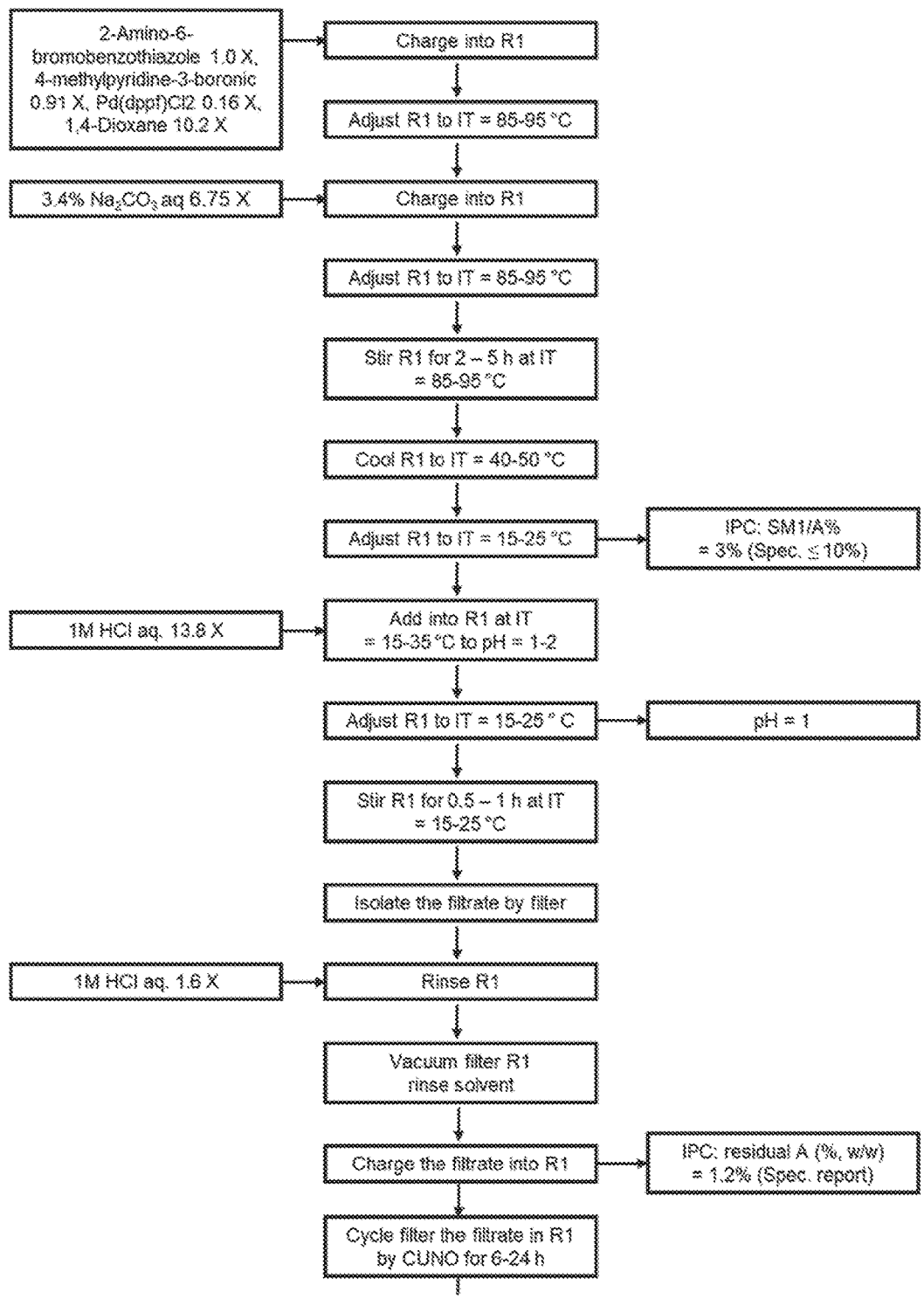
FIG. 1 shows Step 1 for preparing Compound 3.
Figure 1:
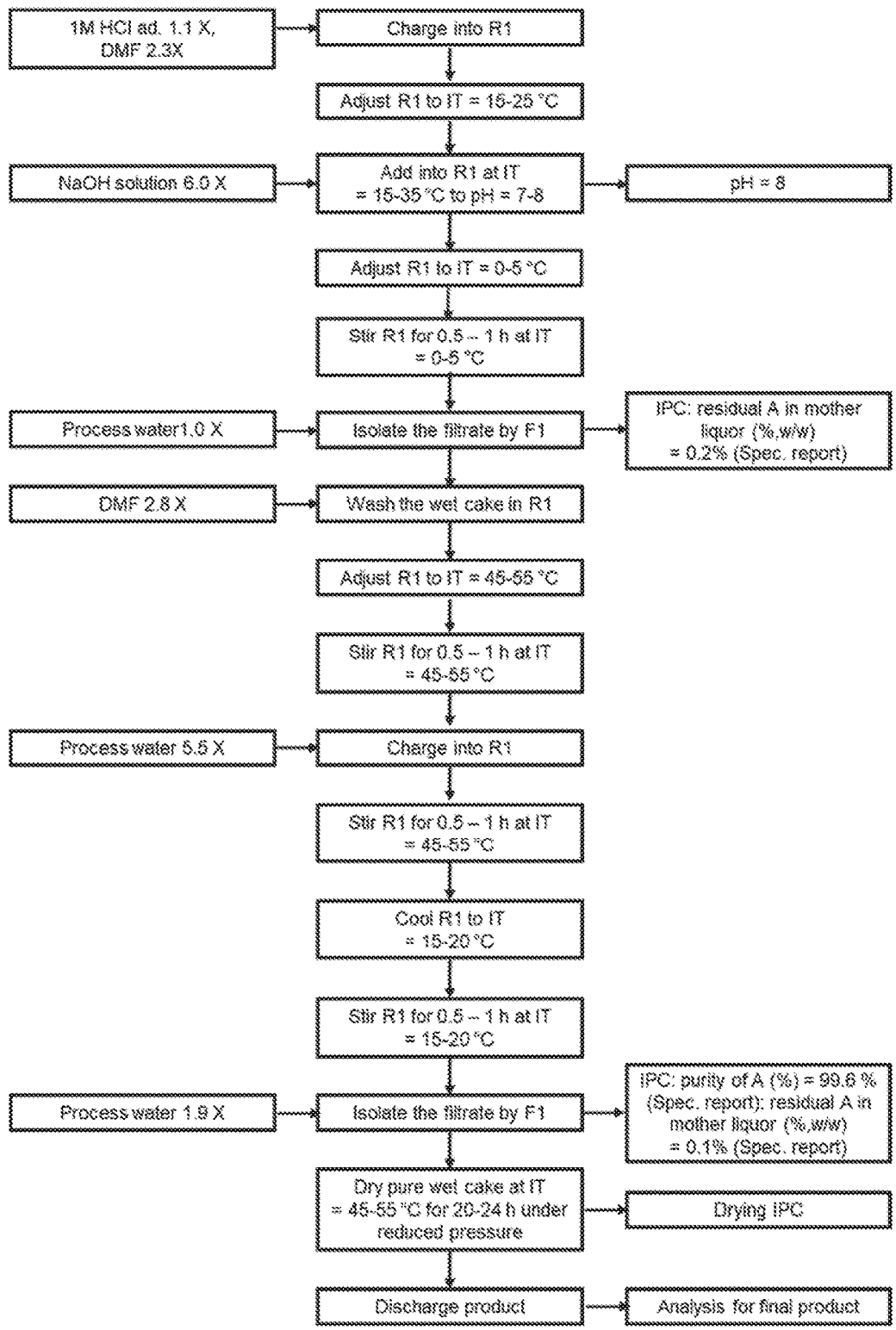
Figure 2:
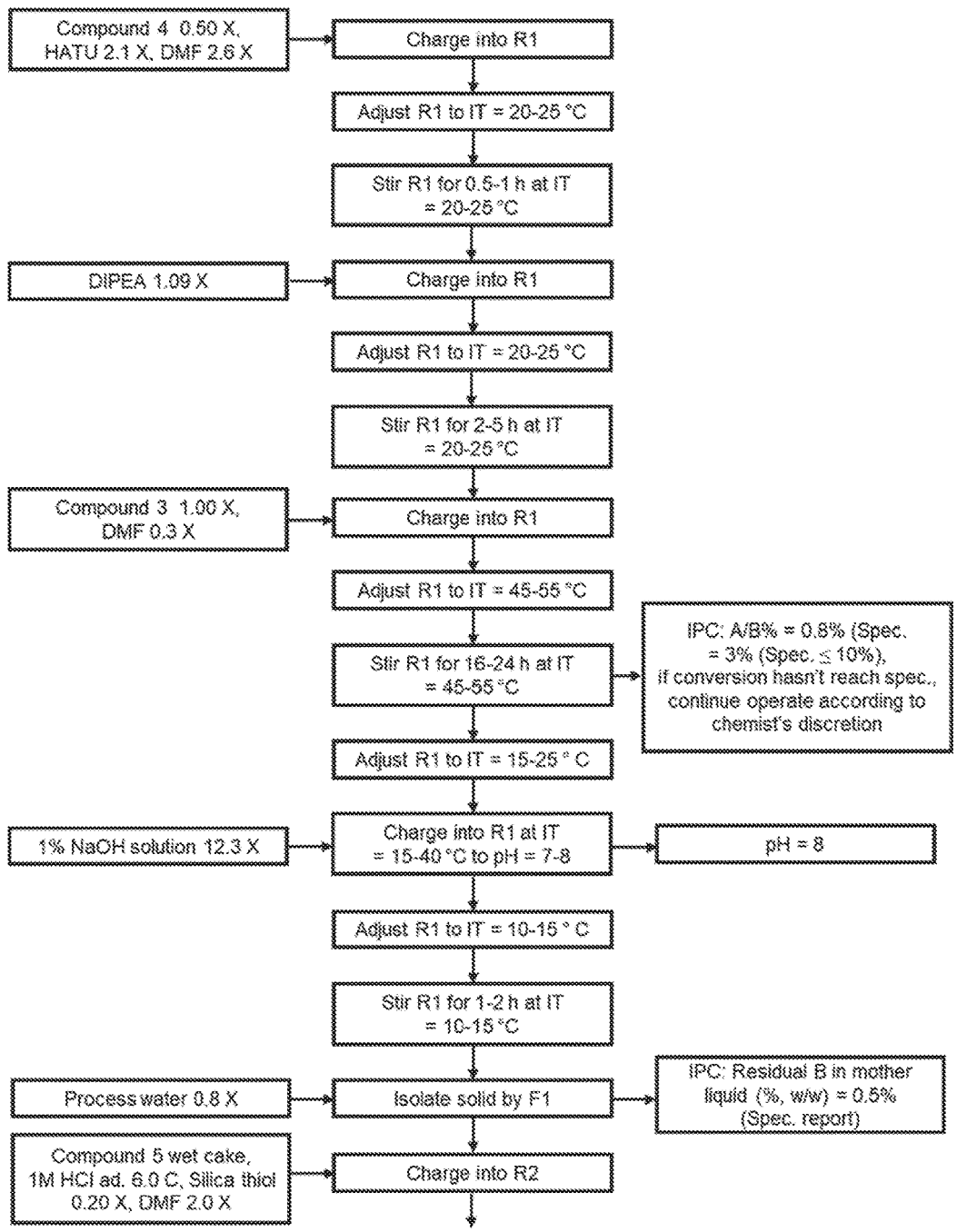
FIG. 2 shows Step 2 for preparing Compound 5.
Figure 2:
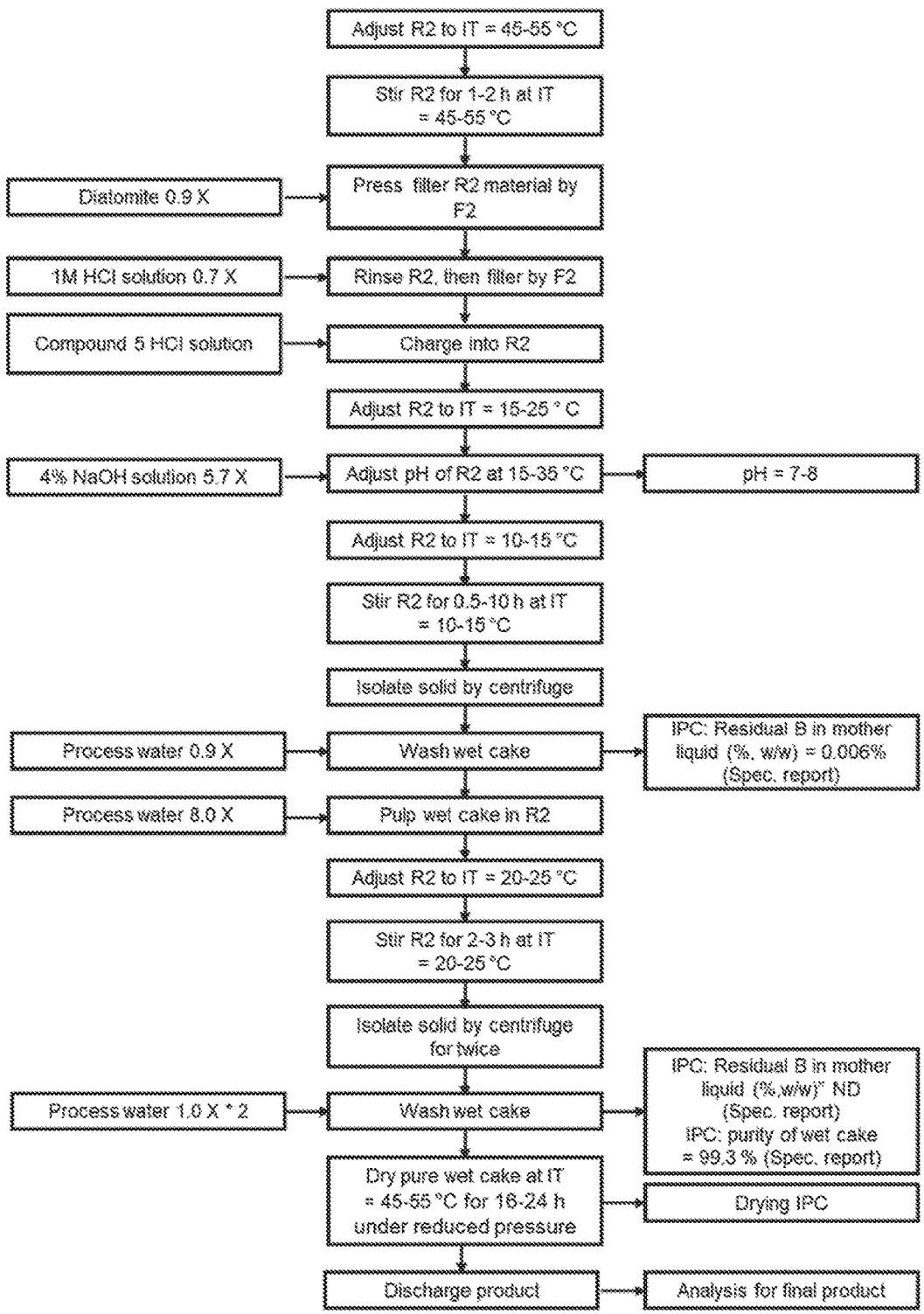
Figure 3:
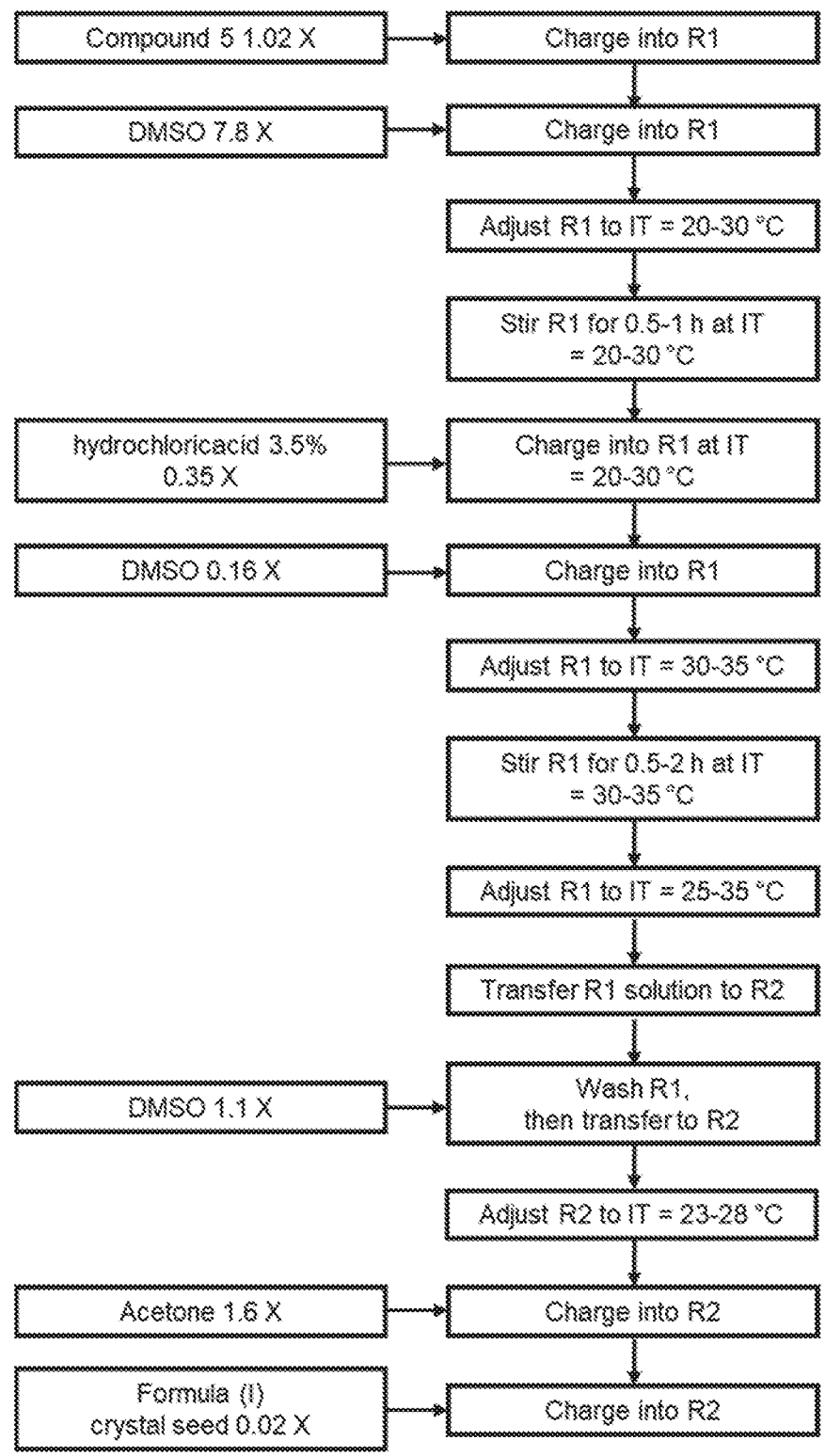
FIG. 3 shows Step 3 for preparing the compound of Formula (I).
Figure 3:
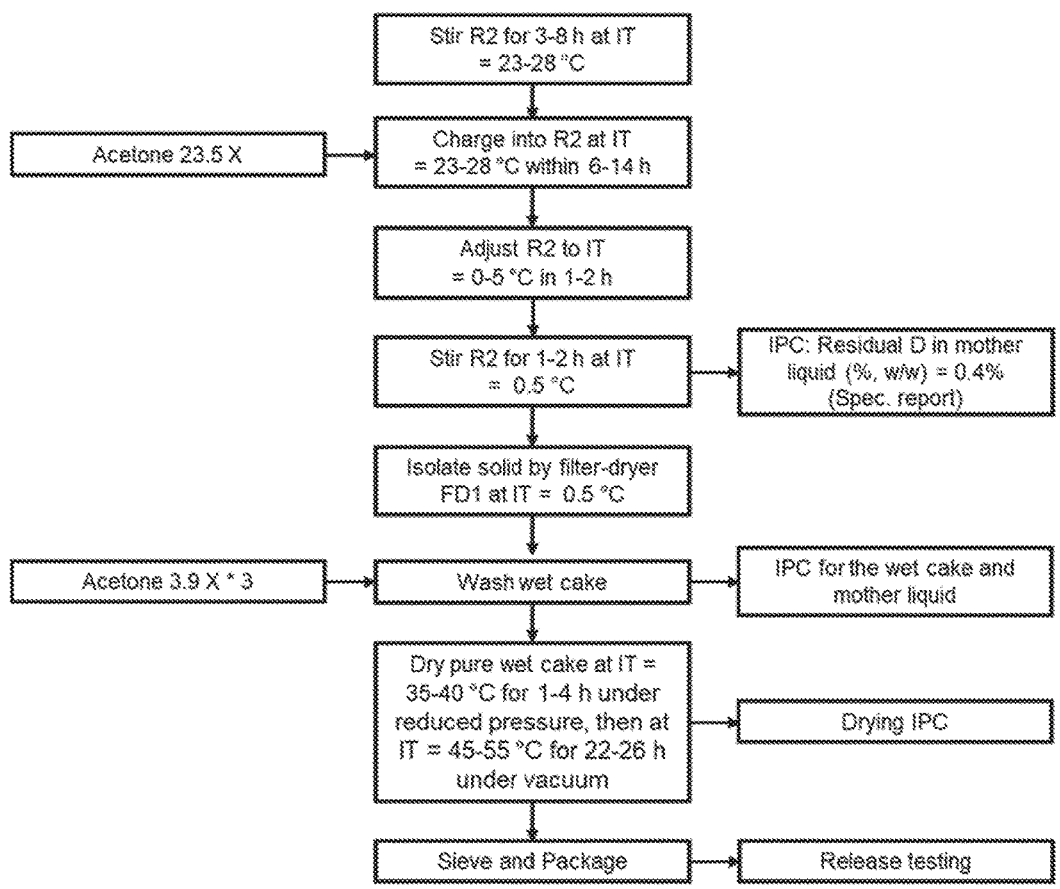

The following description is merely exemplary in nature and is not intended to limit the present disclosure, application, or uses.

Definitions

As used herein, the term "therapeutically effective amount" means when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

As used herein, the term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

In another embodiment, the compounds of Formula (I) are used for modulating the activity of a protein kinase c-abl.

As used herein, the term "modulating", or "modulation" refers to the alteration of the catalytic activity of a protein kinase. In particular, modulating refers to the activation or inhibition of the catalytic activity of a protein kinase, depending on the concentration of the compound or salt to which the protein kinase is exposed or, more preferably, the inhibition of the catalytic activity of a protein kinase. The term "catalytic activity" as used herein refers to the rate of phosphorylation of tyrosine, serine or threonine under the influence, direct or indirect, of a protein kinase.

As used herein, the phrase "compound(s) of this/the disclosure" includes any compound(s) of Formula (I), as well as clathrates, hydrates, solvates, or polymorphs thereof. And even if the term "compound(s) of the disclosure" does not mention its pharmaceutically acceptable sat, the term includes salts thereof. In one embodiment, the compounds of this disclosure include stereochemically pure compounds, e.g., those substantially free (e.g., greater than 85% ee, greater than 90% ee, greater than 95% ee, greater than 97% ee, or greater than 99% ee) of other stereoisomers. That is, if the compounds of Formula (I) according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "salt" includes include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid.

As used herein, the term "sample" includes any compound(s) of Formula (I), as well as clathrates, hydrates, solvates, polymorphs or intermediate compounds thereof.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

Synthesis of Compound 5 and Salt Thereof

In an embodiment, the present disclosure provides a process for preparing Compound 5 or a salt thereof. The method of preparing the compound is further described with an exemplary synthesis for the compound of Formula (I).

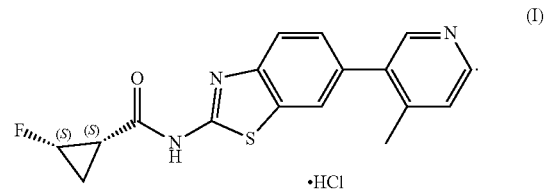

The method of the present disclosure comprises the following Steps 1 and 2 for the synthesis of Compound 5, and optional Step 3 for the synthesis of a salt of Compound 5.

Step 1: reacting Compound 1 as a starting material with Compound 2 in the presence of Pd(dppf)Cl$_2$ and 1,4-dioxane to form Compound 3;

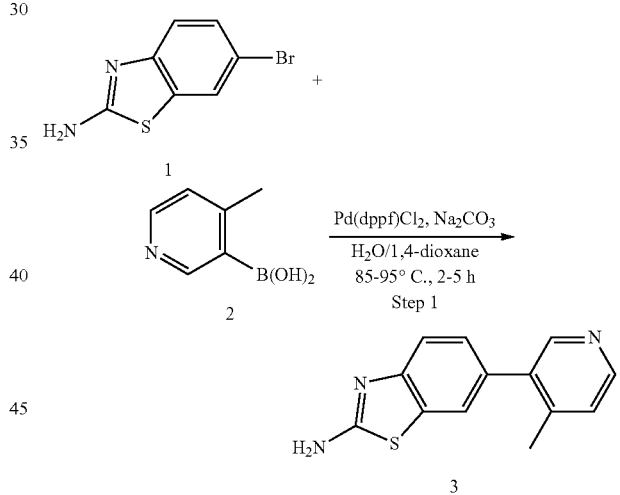

Step 2: reacting Compound 3 with Compound 4 in the presence of HATU and DIPEA to produce Compound 5;

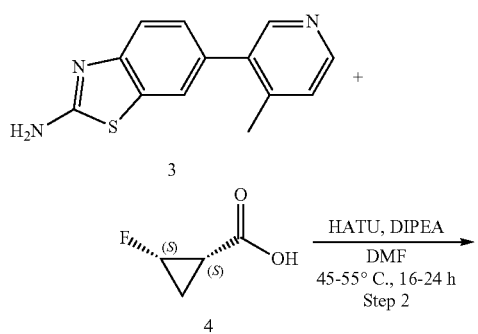

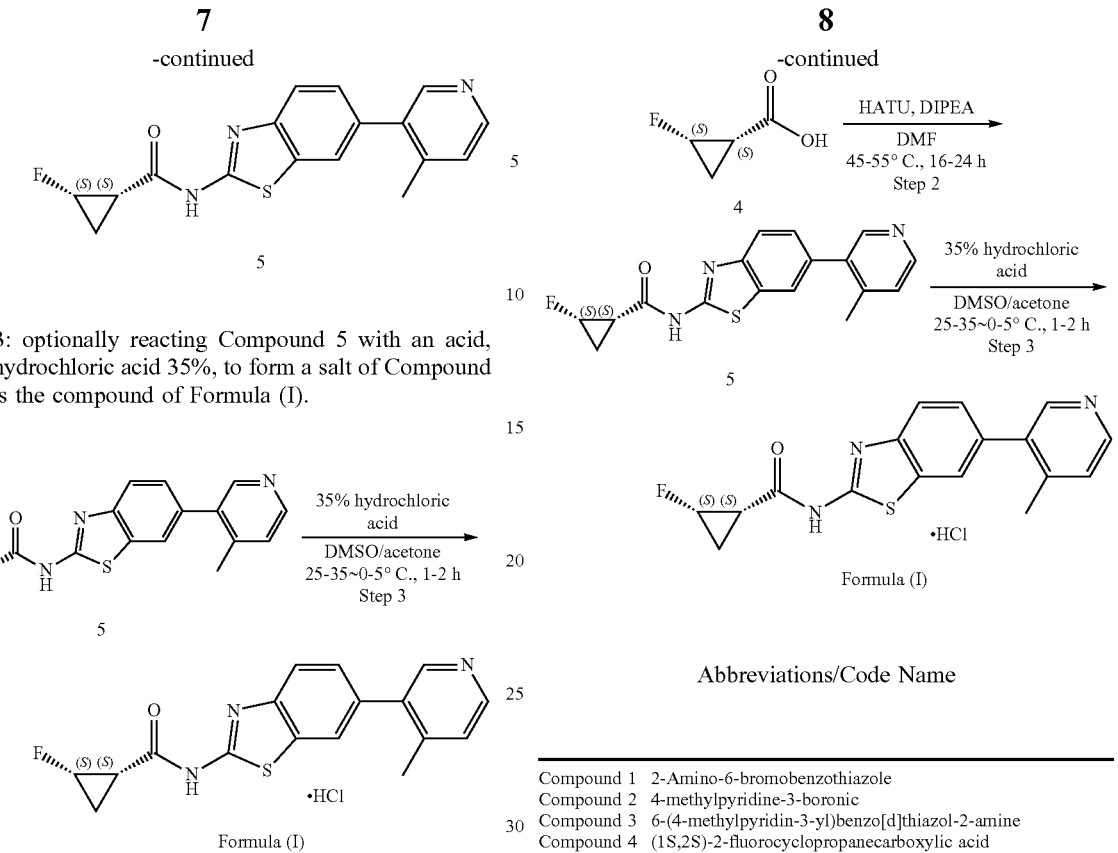

Step 3: optionally reacting Compound 5 with an acid, such as hydrochloric acid 35%, to form a salt of Compound 5 such as the compound of Formula (I).

The compound of Formula (I) was accomplished under cGMP conditions and obtained with 99.9% purity and 100.0%, chiral purity in 84% yield. Through an optimized process, the compound of Formula (I) was obtained in higher yield than original synthetic scheme and process.

1. Synthetic Route

For illustration purposes, the full synthetic route for Formula (I) is depicted in Scheme 1, along with starting materials, intermediates, reagents, solvents and catalysts.

Scheme 1

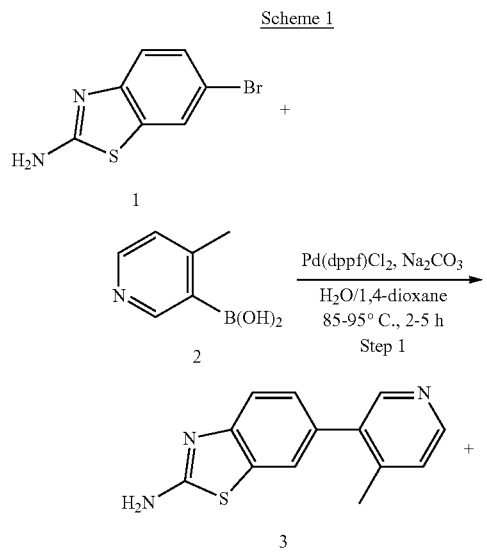

Abbreviations/Code Name

| | |
|---|---|
| Compound 1 | 2-Amino-6-bromobenzothiazole |
| Compound 2 | 4-methylpyridine-3-boronic |
| Compound 3 | 6-(4-methylpyridin-3-yl)benzo[d]thiazol-2-amine |
| Compound 4 | (1S,2S)-2-fluorocyclopropanecarboxylic acid |
| Compound 5 | (1S,2S)-2-fluoro-N-(6-(4-methylpyridin-3-yl)benzo[d]thiazol-2-yl)cyclopropanecarboxamide |
| Formula (I) | (1S,2S)-2-fluoro-N-(6-(4-methylpyridin-3-yl)benzo[d]thiazol-2-yl)cyclopropanecarboxamide hydrochloride |
| Pd(dppf)C$_{12}$ | [1,1'-Bis(diphenylphosphino) ferrocene]dichloropalladium (II) |
| DMF | N,N-Dimethylformamide |
| HATU | O-(7-Azabenzotriazol-1-yl)-N,N,N',N'-tetramethyl uroniumhexafluorophosphate |
| DIPEA | N,N-Diisopropylethylamine |
| DMSO | Dimethyl sulfoxide |
| Pd | Palladium |
| IPC | In-process Control |
| HPLC | High performance liquid chromatography |
| HS-GC | Headspace gas chromatography |
| KF | Karl Fisher |
| X | Unit value |

2. Process Description

1) STEP 1. Preparation of 6-(4-methylpyridin-3-yl)benzo[d]thiazol-2-amine

Compound 1 (6.2 kg, 1.0×), Compound 2 (5.60 kg, 0.90-0.92×), Pd(dppf)Cl$_2$ (1.0 kg, 0.15-0.17×) and 1,4-dioxane (63.4 kg, 10.2-10.5×) were charged to a 500 L glass lining reactor under N$_2$ atmosphere. Reactor was bubbled with N$_2$ for 0.5-1 h., then heated to 85-95° C. 3.4% Na$_2$CO$_3$ solution (41.7 kg, 6.72-6.94×) was charged by dropwise for 30-90 min at 75-95° C., where 3.4% Na$_2$CO$_3$ solution: charging purified water (41.0 kg, 6.5-6.7×) and Na$_2$CO$_3$ (1.5 kg, 0.22-0.24×) into a drum and stirred to visual clear. The mixture was stirred at adjusted temperature of 85-95° C. for 2-5 h., then cooled to 40-50° C. and tested for the residual of Compound 1 (IPC by HPLC: area %≤10%).

1M HCl solution (85.0 kg, 10.0-15.0×) was charged at 15-35° C. until pH reached 1-2, where 1M HCl solution: charging process water (46 kg, 7.0-8.0×) and 35% HCl (13.0 kg, 2.0-2.2×) into a tank, followed with process water (50 kg, 8.0-8.5×), and mixed well. After stirring for 0.5-1 h. at 15-25° C., the mixture was filtered by diatomite filter and the wet cake was rinsed by 1 M HCl solution (10.4 kg, 1-2×) and tested for the residual of Compound 3 (IPC by HPLC: report). The filtrate was decolored by CUNO cycling for 6-24 h. at 15-25° C. 1 M HCl solution (6.8 kg, 1-3×), and DMF (14.0 kg, 2.3-3.5×) were charged to reactor, followed by 12% NaOH solution (37.0 kg, 3.0-6.0×) being charged at 15-35° C. until pH reached 7-8, where 12% NaOH solution: charging process water (32 kg, 4-6×) and NaOH (4.6 kg, 0.4-0.8×) into a drum and stirred to visual clear. The mixture was stirred at adjusted temperature of 0-5° C. for 0.5-1 h., and then was filtered under vacuum in portions. The wet cake was rinsed by process water (6.0 kg, 1.0-2.0×). The mother liquor was tested for the residual of Compound 3 (IPC by HPLC: report).

The above wet cake and DMF (17.0 kg, 2.7-2.9×) were charged to reactor. The mixture was stirred at adjusted temperature of 45-55° C. for 0.5-1 h. After process water (34 kg, 4-6×) being charged, the mixture was continued to be stirred at 45-55° C. for 0.5-1 h., subsequently stirred at adjusted temperature of 15-20° C. for 0.5-1 h. The mixture was filtered under vacuum in portions and rinsed with process water (12 kg, 1.0-2.0×). The wat cake was tested for purity of Compound 3 (IPC by HPLC: report), while the mother liquor was tested for the residual of Compound 3 (IPC by HPLC: report).

The wet cake was dried by a stainless steel dryer under vacuum at 45-55° C. for 20-24 h. until the water content met the specification (IPC: KF (%, w/w)≤0.5%). 3.9 kg intermediate Compound 3 was obtained (purity: 99.6%, assay: 99.2%; Pd: 438 ppm, 1,4-dioxane: 317 ppm, yield: 59%).

2) STEP 2. Preparation of (1S,2S)-2-fluoro-N-(6-(4-methylpyridin-3-yl)benzo[d]thiazol-2-yl)cyclo-propanecarboxamide Compound 4 (1.74 kg, 0.46-0.50×), HATU (7.4 kg, 2.0-2.1×) and DMF (9.0 kg, 2.4-2.6×) were charged to a 100 L glass lining reactor, and were stirred at 20-25° C. for 0.5-1 h. DIPEA (3.8 kg, 1.05-1.10×) was charged to reactor in portions at 20-25° C., and the resulting mixture was stirred for 2-5 h. at this temperature. C171109159-A (3.49 kg, 1.0×) and DMF (1.0 kg, 0.2-0.3×) were charged to the same reactor. The mixture was stirred at adjusted temperature of 45-55° C. for 16-24 h., and then was tested for the residual of Compound 3 (IPC by HPLC: Compound 3/Compound 5≤1.0%).

1% NaOH solution (43.2 kg, 12.0-13.7×) was charged to the reactor at 15-40° C. until the pH reached 7-8, followed by being stirred for 1-2 h. at adjusted temperature of 10-15° C., where 1% NaOH solution: charging process water (45.1 kg, 12.5-13.5×) and liquid sodium hydroxide (1.9 kg, 0.53-0.57×) into a drum and stirred to uniformity. The mixture was filtered in portions and rinsed with process water (2.7 kg, 0.5-1.0×). The wet cake was charged to another 100 L glass lining reactor, followed with 1M HCl solution (21.0 kg, 5.9-6.1×), silica thiol (0.7 kg, 0.18-0.22×) and DMF (7.0 kg, 1.8-2.0×), where 1M HCl solution: charging process water (21.0 kg, 6.1-6.3×) and 35% HCl (2.3 kg, 0.6-0.7×) into a drum and stirred to uniformity. The mixture was stirred at adjusted temperature of 45-55° C. for 1-2 h., and then was filtered by a filter which has added diatomite (3.0 kg, 0.5-1.0×) in advance. 1M HCl solution (2.3 kg, 0.6-0.9×) was charged to rinse reactor and wet cake. The filtrate was collected as Compound 5 HCl solution.

The above Compound 5 HCl solution was charged to the reactor and the temperature of the reactor was adjusted to 15-25° C. 4% NaOH solution (19.6 kg, 5.0-7.9×) was charged until the pH reached 7-8, where 4% NaOH solution: charging process water (22.0 kg, 6.4-6.6×) and liquid sodium hydroxide (3.6 kg, 0.95-1.05×) into a drum and stirred to uniformity. The mixture was stirred for 0.5-10 h. at adjusted temperature of 10-15° C., and centrifuged by a stainless steel centrifuge. After being rinsed by process water (3.0 kg, 0.5-1.0×), the Compound 5 wet cake was charged to the reactor. The mother liquid was tested for the residual of Compound 5 (IPC by HPLC: report). After process water (27.5 kg, 7.8-8.2×) being charged to the reactor, the mixture was stirred at 20-25° C. for 2-3 h. and centrifuged by a stainless steel centrifuge. After being rinsed by process water (3.5 kg, 0.5-1.0×), the wet cake was tested for purity (IPC by HPLC: report), while the mother liquor was tested for the residual of Compound 5 (IPC by HPLC: report).

The above wet cake was dried by a stainless steel dryer under vacuum at 45-55° C. for 16-24 h until the water content met the specification (IPC: KF (%, w/w)≤0.5%). 3.2 kg intermediate Compound 5 was obtained (purity: 99.4%, assay: 98.0%; chiral purity: 99.7%; Pd: <10 ppm, residue on ignition: 0.7%; yield: 66%).

3) STEP 3. Preparation of (1S,2S)-2-fluoro-N-(6-(4-methylpyridin-3-yl)benzo[d]thiazol-2-yl)cyclo-propanecarboxamide hydrochloride; Formula (I)

Compound 5 (6.3 kg, 1.0×) and DMSO (48.6 kg, 7.5-8.0×) were charged to a 250 L glass lining reactor. The mixture was stirred at 20-30° C. for 0.5-1 h. under vacuum. Hydrochloric acid 35% (2.2 kg, 0.34-0.38×) was charged to the suspension by dropwise, followed with 1.0 kg of DMSO. The mixture was stirred at adjusted temperature of 30-35° C. for 0.5-2 h. until the solution was clear, and then was transferred to another 500 L glass lining reactor with the temperature of 25-35° C. by stainless steel cartridge filter. DMSO (6.6 kg, 1.0-1.2×) was charged to rinse the previous reactor and subsequently transferred.

Acetone (10 kg, 1.5-1.7×) was charged to the reactor at 23-28° C., followed with the Formula (I) crystal seed (0.13 kg, 0.019-0.021×). The mixture was stirred for 3-8 h. at 23-28° C. Acetone (146 kg, 22.9-24.5×) was charged to the reactor. The mixture was stirred at adjusted temperature of 0-5° C. for 1-2 h. 20 mL sample was taken to test for the residual of Formula (I). The mixture in the reactor was filtered via a 460 L stainless steel filter-dryer. The wet cake was rinsed with acetone (24 kg, 3.9-4.1×) for several times, and checked for Formula (I) purity and residual DMSO. The mother liquor was tested for the residual of Formula (I).

The wet cake was dried firstly at 35-40° C. under reduced pressure for 1-4 h. without stirring, and then at 45-55° C. under vacuum for 22-26 h. The wet cake was tested for water content, residual solvents and XRPD. The resulting product was held at 20-30° C. for 1 h. at least before packaging. After sieving and packaging, 5.95 kg of Formula (I) compound was obtained (yield: 84%).

3. Elucidation of Formula (I) Structure

The molecular structure of Formula (I) was confirmed through various analyses, including elemental analysis, high resolution mass spectrometry (HRMS), fourier transform infrared (FTIR) spectroscopy, ultraviolet (UV) spectroscopy, nuclear magnetic resonance (NMR) spectroscopy, and X-Ray Powder Diffraction (XRPD). Interpretations of the spectral data are presented below.

Elemental Analysis

C, H, N element analysis was performed on Elementar vario EL III. F and S elements were tested by Ultraviolet spectrometry and Ion chromatography method respectively after combusting sample in oxygen flask. Cl element was tested by silver nitrate titration method. The content of each element is showed in Table 1. The measured content of each element was in line with the theoretical content.

TABLE 1

Elemental Content for Formula (I)

| Element | Content (%) | Theoretical content (%) | Δ (%) |
|---------|-------------|------------------------|-------|
| C | 56.09 | 56.12 | 0.03 |
| H | 4.29 | 4.16 | −0.13 |
| N | 11.43 | 11.55 | 0.12 |
| F | 5.19 | 5.72 | 0.03 |
| S | 8.43 | 8.81 | 0.38 |
| Cl | 9.73 | 9.74 | 0.01 |

High Resolution Mass Spectrometry (HRMS)

HRMS analysis was performed on the Waters H-Class high performance liquid chromatography with quadruple mass spectrometry with positive ion mode.

Figure 4:
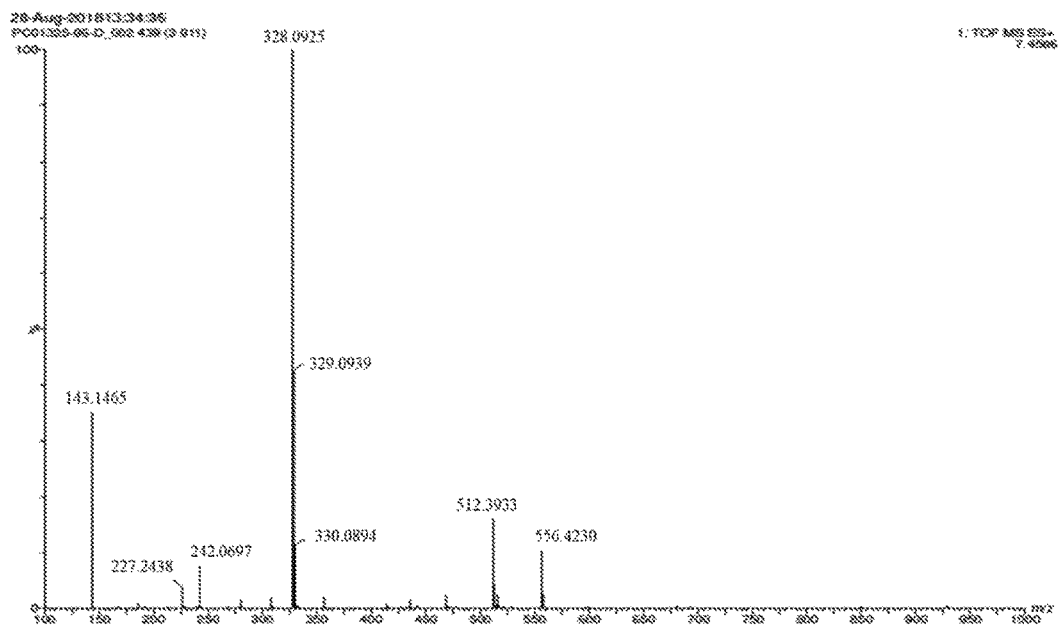
FIG. 4 shows mass results for the compound of Formula (I). The sample yielded three strong positive ions as demonstrated in the spectra with pseudo molecular ion [M+H]$^+$ observed at m/z 328.0925, 329.0939, 330.0894 corresponding to the pronated free base [calculated m/z, 327.08 (100.0%); 328.09(18.6%); 329.08(4.7%)]
Figure 4:
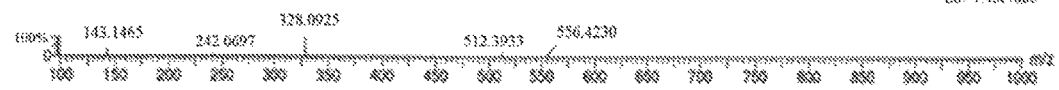

The sample yielded three strong positive ions as demonstrated in the spectra (FIG. 4) with pseudo molecular ion $[M+H]^+$ observed at m/z 328.0925, 329.0939, 330.0894 corresponding to the pronated free base [calculated m/z, 327.08(100.0%); 328.09(18.6%); 329.08(4.7%)]. The elemental composition result is shown in Table 1. The data was consistent with the molecular formula proposed for the free base of Formula (I).

Fourier Transform Infrared (FTIR) Spectroscopy

The Fourier Transform Infrared (FT-IR) analysis was performed on a NICOLET iS10 FT-IR spectrometer using KBr plate. The spectrum was recorded at a resolution of 4 $cm^{-1}$ and a sum of 32 scans, with the subtraction of background.

Figure 5:
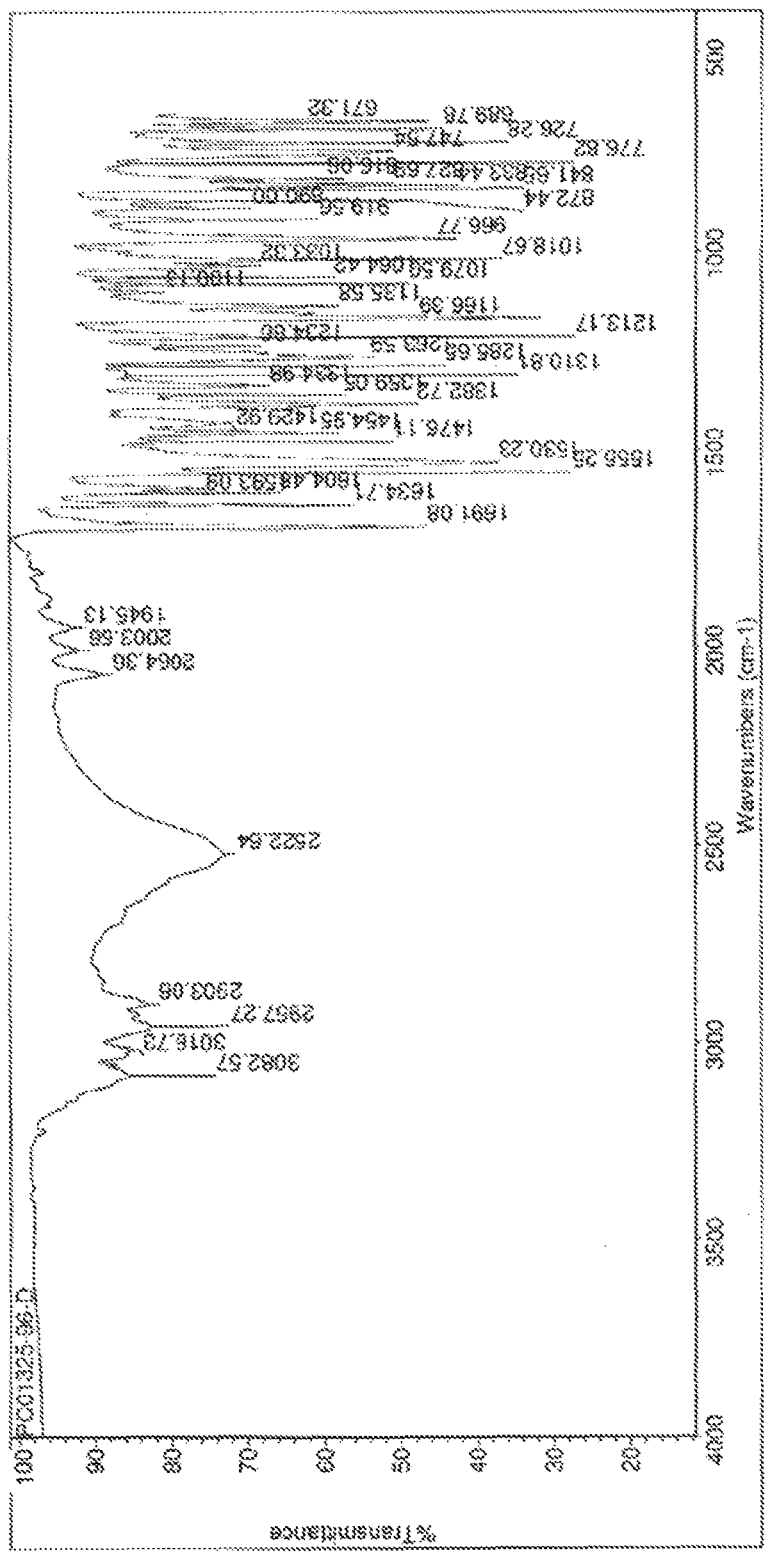
FIG. 5 shows FT-IR spectra of the compound of Formula (I), confirming that characteristic absorption bands are consistent with the functional groups present in the proposed structure for Formula (I) compound.

The IR spectrum of Formula (I) in FIG. 5 shows that characteristic absorption bands are consistent with the functional groups present in the proposed structure for Formula (I). The assignments of the major absorption bands were presented in Table 2.

TABLE 2

Infrared Absorption Spectral Assignment for Formula (I)

| Wave number ($cm^{-1}$) | Assignment |
|---|---|
| 3082-2903 | C—H anti-symmetric and symmetric stretches of the $CH_3$, $CH_2$, CH and FC-H groups. |
| 2522 | N—H stretch in the amide group. |
| 2064-1945 | Harmonic waves of the heterocyclic ring. |
| 1691 | C=O stretch in the amide group. |
| 1634-1593 | S—C=N stretch in the heterocyclic ring. |
| 1555-1530 | C—C stretch in the heterocyclic ring. |
| 1476-1310 | Bending, deformation, and scissoring vibrations of the $CH_3$, $CH_2$, CH and FC—H groups. |
| 1285-1018 | C—F, C—N stretches in the FC—H and amide groups. |
| 966-671 | Out-of-plane C-H bending vibrations in the heterocyclic ring. |

Ultraviolet (UV) Spectroscopy

The concentration of sample solution for analysis was 0.005 mg/mL of Formula (I), and the diluent was Acetonitrile: $H_2O$=1:1, v/v.

Figure 6:
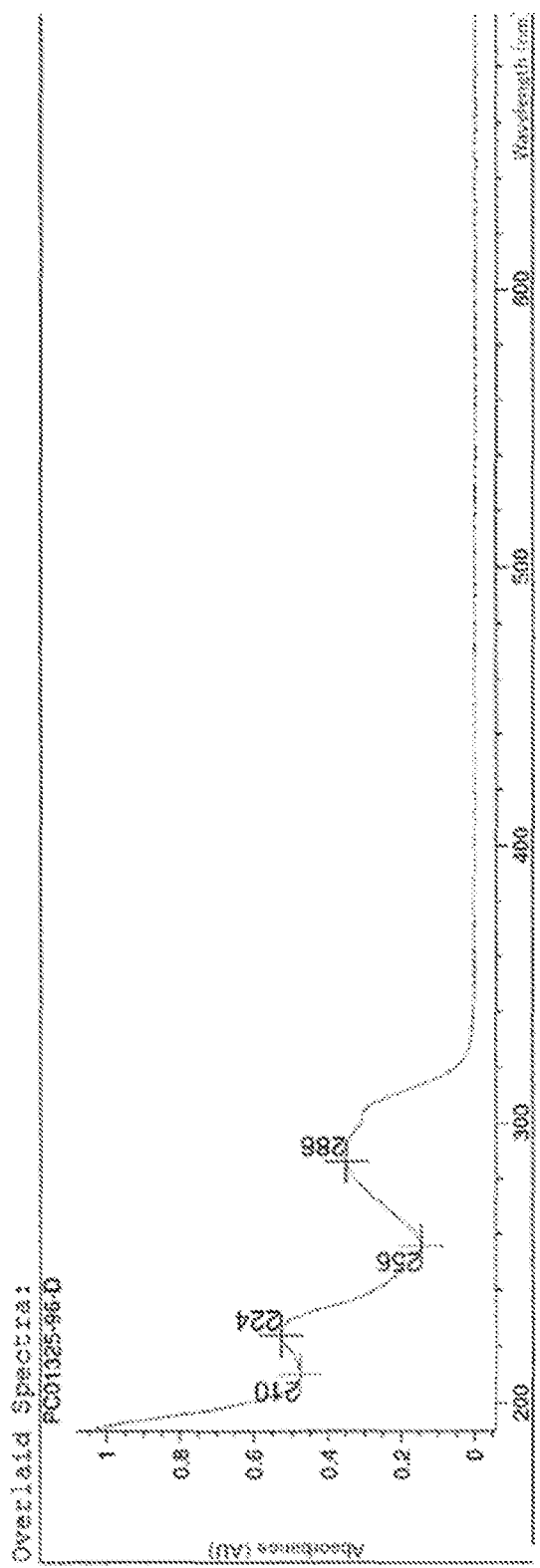
FIG. 6 shows Ultraviolet Spectroscopy (UV) analysis performed on Agilent UV-Vis8453. The wavelength range was 190 nm to 700 nm.

The Ultraviolet Spectroscopy (UV) analysis was performed on Agilent UV-Vis8453. The wavelength range was 190 nm-700 nm. UV Spectrum of Formula (I) is shown in FIG. 6. It can be seen from the figure that Formula (I) has two absorption peaks at 224 nm and 286 nm.

Nuclear Magnetic Resonance (NMR) Spectroscopy

A Bruker AVANCEIII 400 MHz NMR spectrometer equipped with a Bruker 5 mm PABBO Z-gradient probe, and supported by TOPSPIN 3.5 software, was used to collect 1-dimensional (1D) proton and carbon NMR data at room temperature.

The sample was prepared by dissolving 20 mg of Formula (I) compound in 0.7 mL of DMSO-$d_6$, then transferring the solution to a NMR tube for 1D NMR test.

Figure 7:
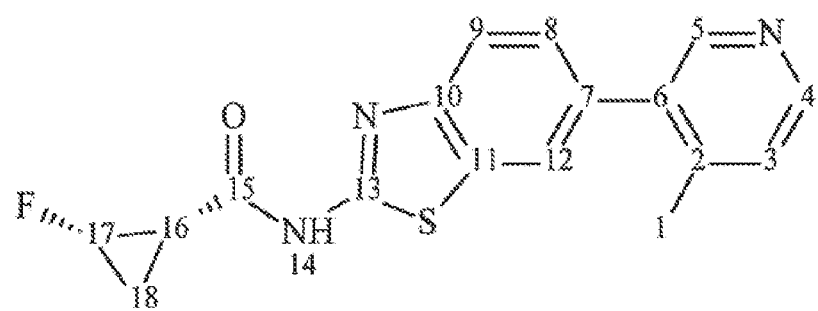
FIG. 7 illustrates the numbered structure of Formula (I) compound.
Figure 8:
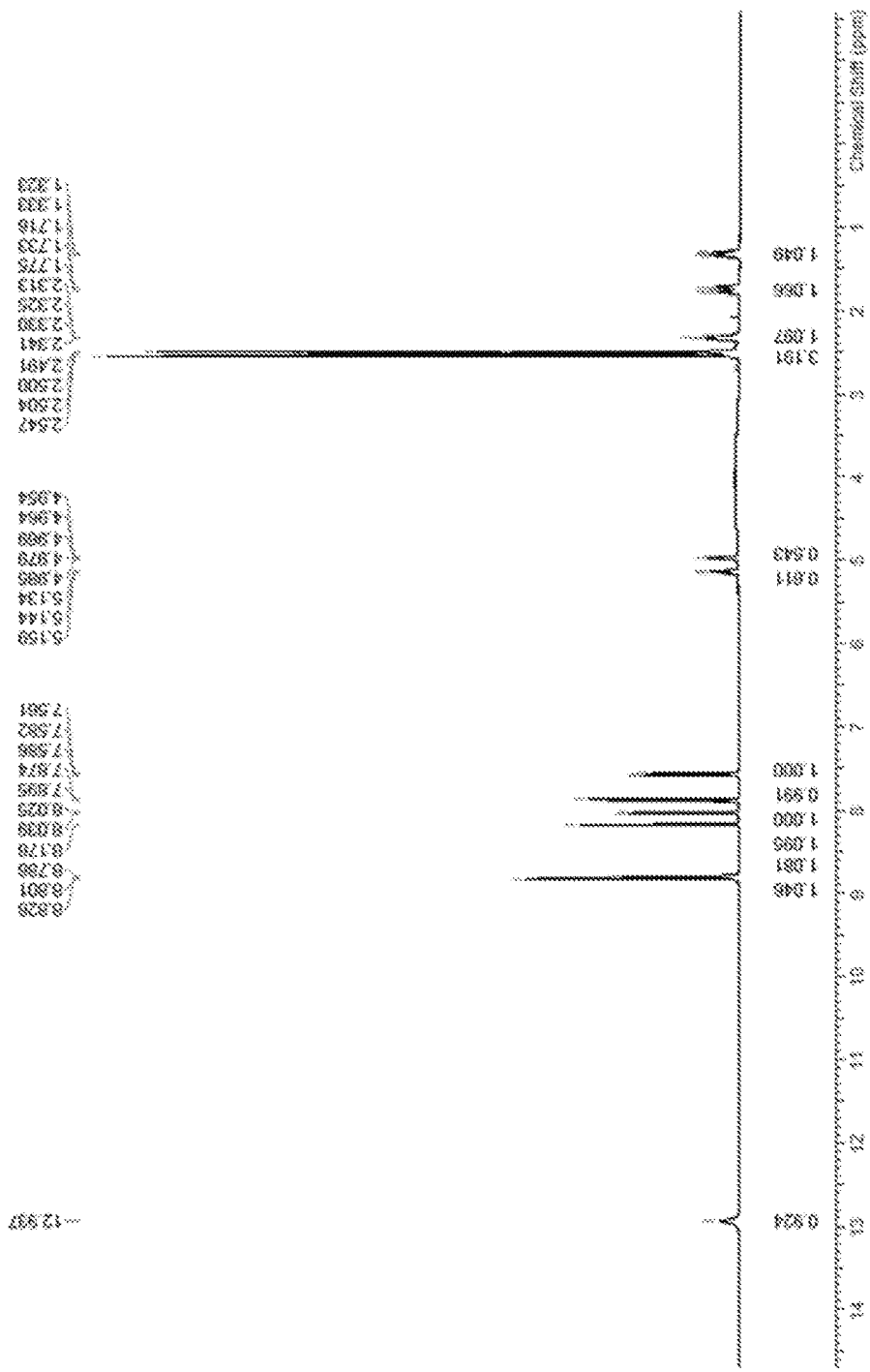
FIG. 8 shows the $^1$H NMR spectra of Formula (I) compound.
Figure 9:
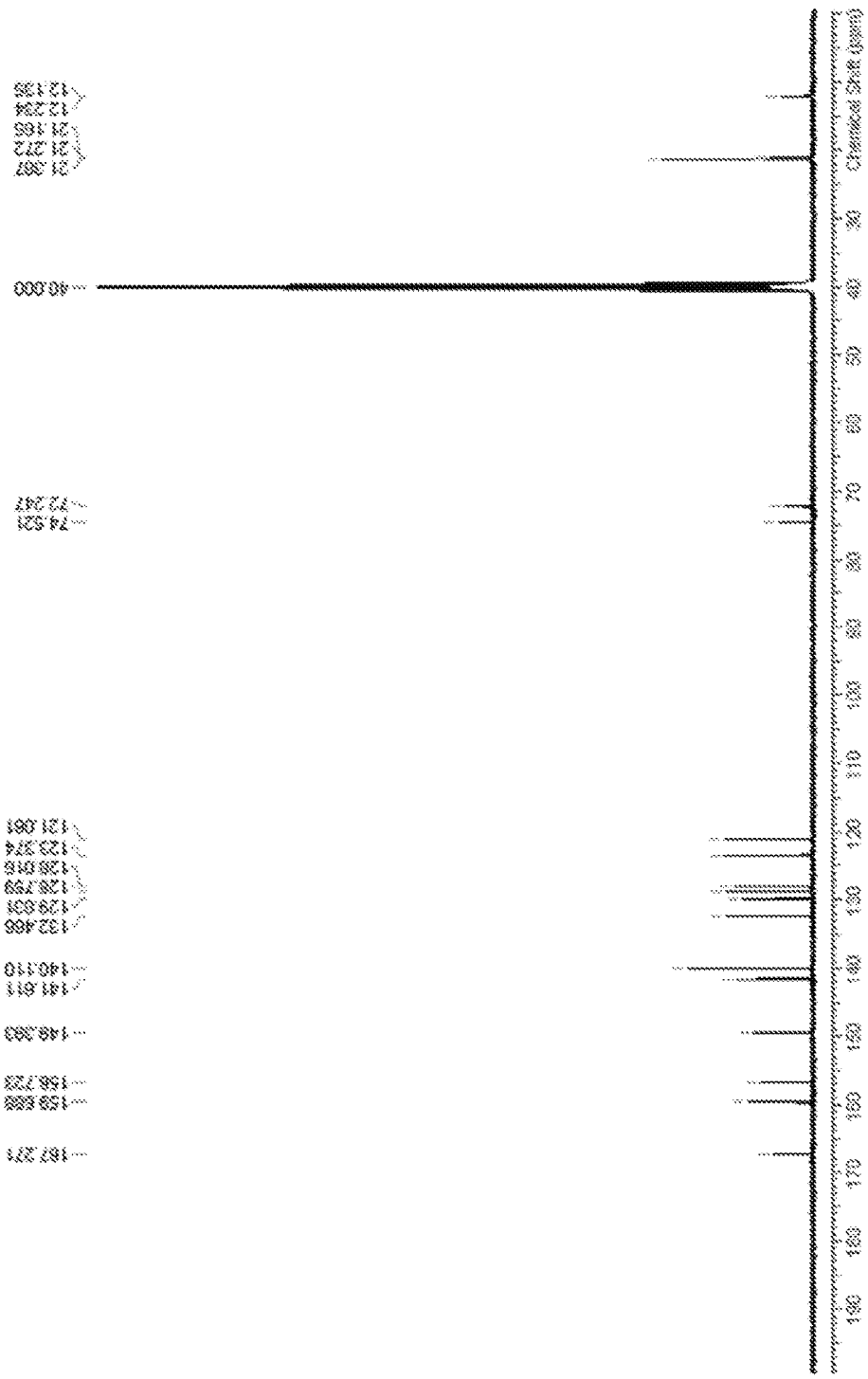
FIG. 9 shows the $^{13}$C NMR spectra of Formula (I) compound.

The numbered structure of Formula (I) compound is shown in FIG. 7. The $^1H$ and $^{13}C$ NMR spectra for Formula (I) are shown from FIGS. 8 to 9, respectively. The assignments of chemical shifts (in ppm) of proton and carbon are tabulated in Table 3.

TABLE 3

Chemical Shift Assignment for Formula (I) in DMSO-$d_6$

| Assignment[a] | Type | $\delta_C$[b] (ppm) | $\delta_H$[c] (ppm) | Relative Intensity[d] |
|---|---|---|---|---|
| 1 | $CH_3$ | 21.4 | 2.55 (s) | 3H |
| 2 | C | 156.7 | N/A | N/A |
| 3 | CH | 128.8 | 8.03 (d, J = 5.88 Hz) | 1H |
| 4 | CH | 140.1 (o) | 8.79 (d, J = 5.96 Hz) | 1H |
| 5 | CH | 141.6 | 8.83 (s) | 1H |
| 6 | C | 129.8 | N/A | N/A |
| 7 | C | 132.5 | N/A | N/A |
| 8 | CH | 128.0 | 7.57 (dd, J = 8.32 Hz, J = 1.84 Hz,) | 1H |
| 9 | CH | 121.1 | 7.88 (d, J = 8.44 Hz) | 1H |
| 10 | C | 149.4 | N/A | N/A |
| 11 | C | 140.1 (o) | N/A | N/A |
| 12 | CH | 123.4 | 8.17 (d, J = 1.56 Hz) | 1H |
| 13 | C | 159.7 | N/A | N/A |
| 14 | NH | N/A | 12.94 (s) | 1H |
| 15 | C | 167.3 | N/A | N/A |
| 16 | CH | 21.3, 21.2 | 2.32 (m) | 1H |
| 17 | CH | 74.5, 72.3 | 5.14 (m), 4.97 (m) | 1H |
| 18 | $CH_2$ | 12.2, 12.1 | 1.75 (m), 1.33 (m) | 2H |

[a]See Figure 7
[b]$^{13}C$ NMR chemical shift data were obtained from the 1-D carbon NMR experiment. Centerline of the carbon resonance due to the DMSO-$d_6$, was used as an internal reference at 40.0 ppm.
[c]$^1H$ NMR chemical shift data were obtained from the 1-D proton NMR spectrum. The residual solvent resonance of the DMSO-$d_6$ was used as an internal reference at 2.50 ppm.
[d]Relative integrated intensities of proton resonances were measured from the 1-D proton NMR spectrum.
s = singlet,
d = doublet,
t = triplet,
m = multiplet,
o = overlay,
N/A = Not applicable X-Ray Powder Diffraction (XRPD)

Figure 10:
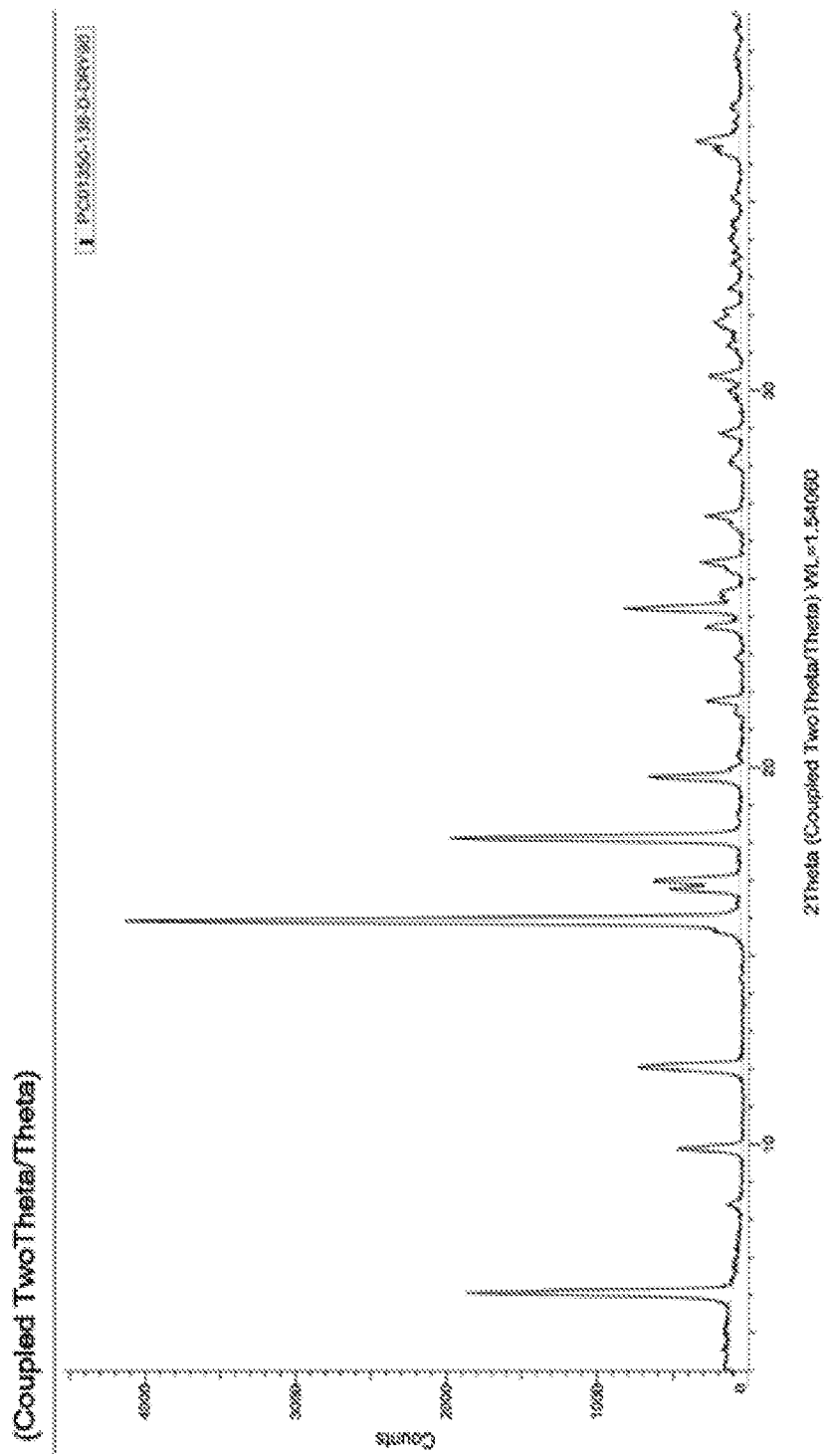
FIG. 10 shows the XRPD pattern of Formula (I) compound.

The XRPD pattern of Formula (I) compound is presented in FIG. 10.

Thermogravimetric Analysis (TGA) and Differential Scanning Calorimetry (DSC)

Figure 11:
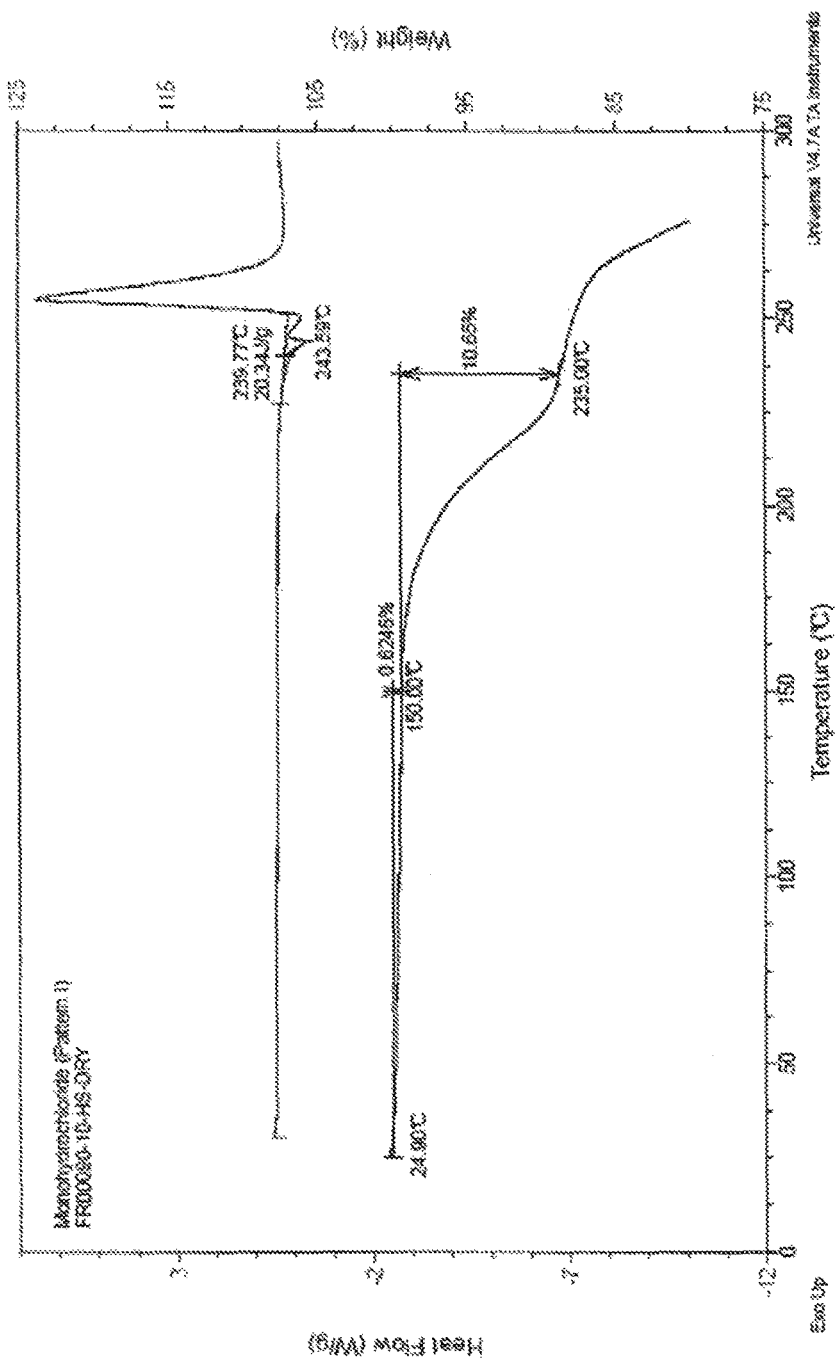
FIG. 11 shows DSC and TGA scans overlay of Formula (I) compound.

DSC and TGA scans overlay of Formula (I) are showed in FIG. 11. DSC result showed two continuous endothermic peaks at the onset of 239.8° C. and the peak of 243.6° C., immediately followed by a big exothermic peak.

TGA result showed a 0.62% weight loss from 25° C. to 150° C. and a 10.65% weight loss from 150° C. to 235° C.

What is claimed is:

1. A process for preparing (1S,2S)-2-fluoro-N-(6-(4-methylpyridin-3-yl)benzo[d]thiazol-2-yl) cyclopropanecarboxamide, comprising:

(i) reacting 2-Amino-6-bromobenzothiazole with 4-methylpyridine-3-boronic in the presence of Pd(dppf)Cl$_2$ and 1,4-dioxane; and (ii) reacting 6-(4-methylpyridin-3-yl)benzo[d]thiazol-2-amine with (1S,2S)-2-fluorocyclopropanecarboxylic acid in the presence of HATU and DIPEA.

2. The process of claim 1, wherein step (i) is carried out at about 85-95° C.

3. The process of claim 1, wherein Na$_2$CO$_3$ solution is added to step (i).

4. The process of claim 1, wherein step (ii) is carried out at about 45-55° C.

5. The process of claim 1, wherein DMF is added to step (ii).

6. A process for preparing a salt of (1 S,2S)-2-fluoro-N-(6-(4-methylpyridin-3-yl)benzo[d]thiazol-2-yl) cyclopropanecarboxamide, comprising:

(i) reacting 2-Amino-6-bromobenzothiazole with 4-methylpyridine-3-boronic in the presence of Pd(dppf)Cl$_2$ and 1,4-dioxane;

(ii) reacting 6-(4-methylpyridin-3-yl)benzo[d]thiazol-2-amine with (1 S,2S)-2-fluorocyclopropanecarboxylic acid in the presence of HATU and DIPEA; and (iii) reacting (1S,2S)-2-fluoro-N-(6-(4-methylpyridin-3-yl)benzo[d]thiazol-2-yl) cyclopropanecarboxamide with an acid.

7. The process of claim 6, wherein the salt is (1 S,2S)-2-fluoro-N-(6-(4-methylpyridin-3-yl)benzo[d]thiazol-2-yl) cyclopropanecarboxamide hydrochloride.

8. The process of claim 7, wherein the acid is hydrochloric acid 35%.

9. The process of claim 6, wherein step (i) is carried out at about 85-95° C.

10. The process of claim 6, wherein Na$_2$CO$_3$ solution is added to step (i).

11. The process of claim 1, wherein step (ii) is carried out at about 45-55° C.

12. The process of claim 1, wherein DMF is added to step (ii).

13. The process of claim 6, wherein DMSO is added to step (iii).

14. The process of claim 6, wherein acetone is added to step (iii).

* * * * *